US005901200A

United States Patent [19]

Krause

[11] Patent Number: 5,901,200

[45] Date of Patent: May 4, 1999

[54] X-RAY EXAMINATION APPARATUS CONVERTIBLE FOR MOBILE OR STATIONARY MOUNTING

[75] Inventor: Hartmut Krause, Erlangen, Germany

[73] Assignee: Siemens Aktiengesellschaft, Munich, Germany

[21] Appl. No.: 08/882,037

[22] Filed: Jun. 25, 1997

[30] Foreign Application Priority Data

Jun. 25, 1996 [DE] Germany ............................ 19625407

[51] Int. Cl.[6] ........................................ A61B 6/02

[52] U.S. Cl. .............................. 378/198; 378/197

[58] Field of Search ........................ 378/198, 197, 378/193

[56] References Cited

U.S. PATENT DOCUMENTS

| | | | |
|---|---|---|---|
| 3,702,935 | 11/1972 | Carey et al. | 378/198 X |
| 5,521,957 | 5/1996 | Hansen | 378/198 |
| 5,627,873 | 5/1997 | Hanover et al. | 378/198 X |

FOREIGN PATENT DOCUMENTS

| | | | |
|---|---|---|---|
| 231 969 | 8/1987 | European Pat. Off. | 378/198 |
| 4-190224 | 7/1992 | Japan | 378/198 |

OTHER PUBLICATIONS

Siemens Brochure for SIREMOBIL 2000 Mobile X–ray Imaging Apparatus No date.

Siemens Brochure for ARCOSKOP 100 OP–III C–arm Stationary Imaging Apparatus No date.

*Primary Examiner*—David P. Porta

*Attorney, Agent, or Firm*—Hill & Simpson

[57] ABSTRACT

An X-ray examination apparatus has an X-ray diagnostic assembly with a carrier having an X-ray source and a beam receiver disposed at opposite ends of the carrier, and a first coupling part connected to the carrier, a mobile base unit containing a plurality of components for operating said X-ray diagnostic assembly and having a second coupling part, and at least one support for stationary mounting in an examination room, having a third coupling part. The first coupling part of the carrier can be optionally connected to the second coupling part, for producing a mobile diagnostic apparatus, or to the third coupling part for producing a stationary diagnostic apparatus. When the first and third coupling parts are engaged and the X-ray diagnostic assembly is used as a stationary apparatus, the mobile base unit can be moved to the side, so that it does not hinder access to the stationary apparatus, but the components contained in the base unit remain connected to the X-ray diagnostic assembly.

6 Claims, 3 Drawing Sheets

1
2
3
4
5
6
7
8
9
10
11
12
13
32
33
35
A
B
α
γ

3
2
A
4
8
9
5
31
15
34
18
17
C
16
B
11
19
14
12
36
1

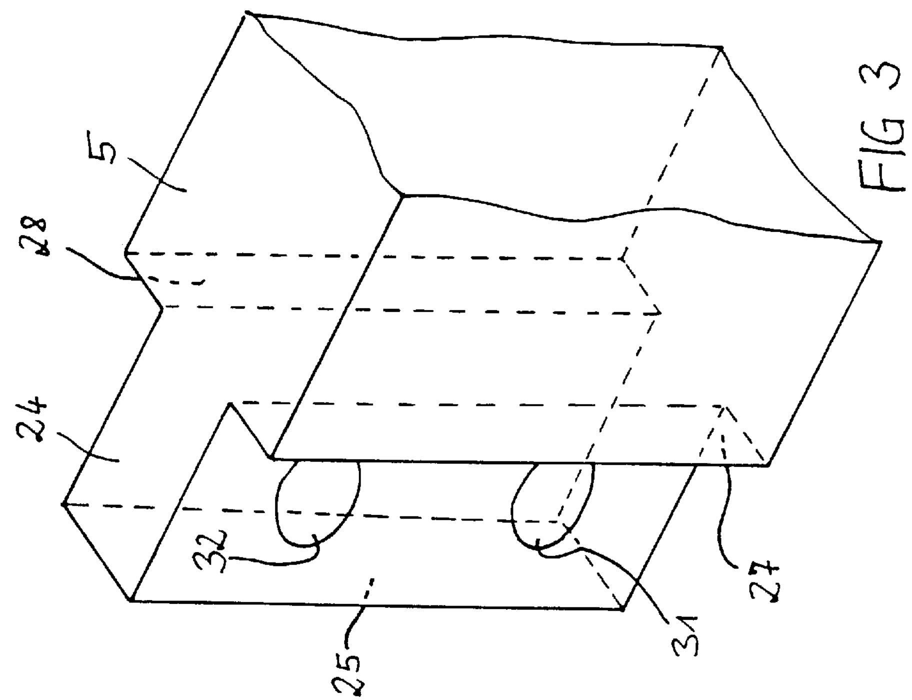
5
28
24
32
25
31
27
FIG 3
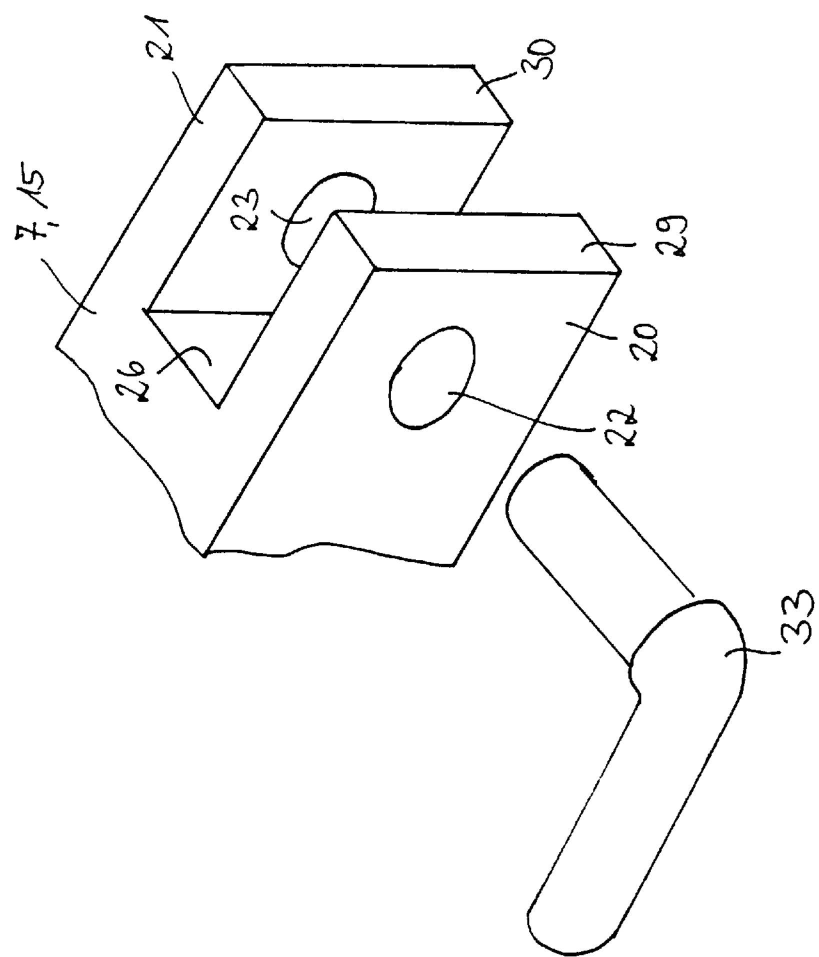
21
30
7,15
23
29
26
20
22
33

X-RAY EXAMINATION APPARATUS CONVERTIBLE FOR MOBILE OR STATIONARY MOUNTING

BACKGROUND OF THE INVENTION

1. Field of the Invention

The present invention is directed to an X-ray examination apparatus of the type having an X-ray diagnostic assembly with a source of X-ray radiation and a beam receiver, attached opposite one another on a carrier provided with a coupling part which attaches the assembly to a mobile base unit that houses components required for the operation of the X-ray diagnostic assembly and to which the carrier is attached.

2. Description of the Prior Art

An X-ray examination apparatus of the above type is known and marketed e.g. by the Siemens company designated "SIREMOBIL 2000." Apparatuses of this type usually have a C-shaped carrier for the X-ray source and radiation receiver (detector), and are thus often referred to as C-arm X-ray devices. Due to their mobility, X-ray examination apparatuses of this sort are used mostly in operating rooms and treatment rooms, since their mobility makes it easy to move them to an operating table or treatment table, and to orient them as required relative to a patient lying on the operation table or treatment table.

The fact that accessibility to the patient is disturbed by the presence of the base unit, however, is often cited as a disadvantage of equipment of this sort.

SUMMARY OF THE INVENTION

An object of the present invention is thus to provide an X-ray diagnostic apparatus of the type which allows improved access to the patient when necessary, in a manner unhindered by the base unit.

The above object is achieved in accordance with the principles of the present invention in an X-ray examination apparatus which includes an X-ray diagnostic assembly having a carrier with an X-ray source and a beam receiver mounted at opposite ends thereof, and having a first coupling part, a mobile base unit containing components electrically connected to said X-ray diagnostic assembly for operating said X-ray diagnostic assembly, and having a second coupling releasably engageable with said first coupling part, and at least one support for stationary mounting of the X-ray diagnostic assembly in an examination room, having a third coupling part which is also releasably engageable with the first coupling part. The carrier can thus be optionally coupled to the second coupling part, in order to form an overall mobile diagnostic apparatus, or can be coupled to the third coupling part, in order to form an overall stationary examination apparatus.

Depending on the requirements of the moment, the inventive X-ray examination apparatus can be used as a conventional mobile X-ray apparatus, or as a stationary (room-mounted) X-ray apparatus with a support, whereby in the latter case the access to the patient is not hindered by the base unit.

Stationary X-ray examination apparatuses, which have an X-ray diagnostic assembly with an X-ray source and a beam receiver, arranged opposite one another on a carrier attached to a support, are also known, and have been marketed by the Siemens company designated as "ARCOSKOP."

The inventive X-ray examination apparatus also reduces the investment in equipment which must be made by the customer. In larger hospitals with several operating rooms and/or treatment rooms, a number of mobile X-ray examination apparatuses of the known types described above are generally present, as well as a number of the known stationary type. Experience has shown that, as a rule, not all such X-ray examination apparatuses are used at the same time. This is undesirable with respect to the cost problemats which currently exist in the health services field, since the acquisition of both a mobile and of a stationary X-ray apparatus incurs a duplicated cost for the X-ray diagnostic assembly and the base unit containing the equipment required for the operation of the X-ray diagnostic apparatus. In contrast, in the case of the inventive X-ray examination apparatus, this cost is incurred only once. Since in comparison to a conventional mobile X-ray apparatus only the expense of the coupling parts and the support(s) is incurred as an additional cost, the reduction of the investment requirement is significant.

In this connection, it is also important that several stationary supports arranged in different rooms can each be provided with a third coupling part, so that it is possible, with a reduced investment expense, to be able to conduct X-ray diagnostic examinations by means of a single X-ray examination assembly that can be converted to a stationary arrangement in each of several rooms (though not simultaneously).

According to a variant of the invention, an articulated linkage means is provided between the first coupling part and the carrier, for positioning the carrier relative to the first coupling part. This allows the articulated linkage to be used both for attaching the carrier to the base unit and to the support, resulting in a further cost reduction.

According to a preferred embodiment of the invention, the beam receiver of the X-ray examination assembly is formed by an X-ray image intensifier to which an X-ray image intensifier video chain with at least one monitor is allocated, and the monitor is attached to the base unit. Thus, no special equipment is required for placement of the monitor.

In an embodiment wherein monitor is detachable from the base unit, the support includes a mount for the monitor. The possibility then exists of attaching the monitor to the mount of the support provided for this purpose, in order to be able to position it advantageously for viewing, without having to situate the base unit immediately beside the operating table or the treatment table.

In another embodiment of the invention the second and the third coupling parts are of identical construction in their respective regions provided for cooperation with the first coupling part. In this way, a simple construction of the first coupling part is enabled.

DESCRIPTION OF THE DRAWINGS

FIG. 3 shows a detail of the inventive X-ray examination apparatus, in a perspective view.

DESCRIPTION OF THE PREFERRED EMBODIMENTS

Figure 1:
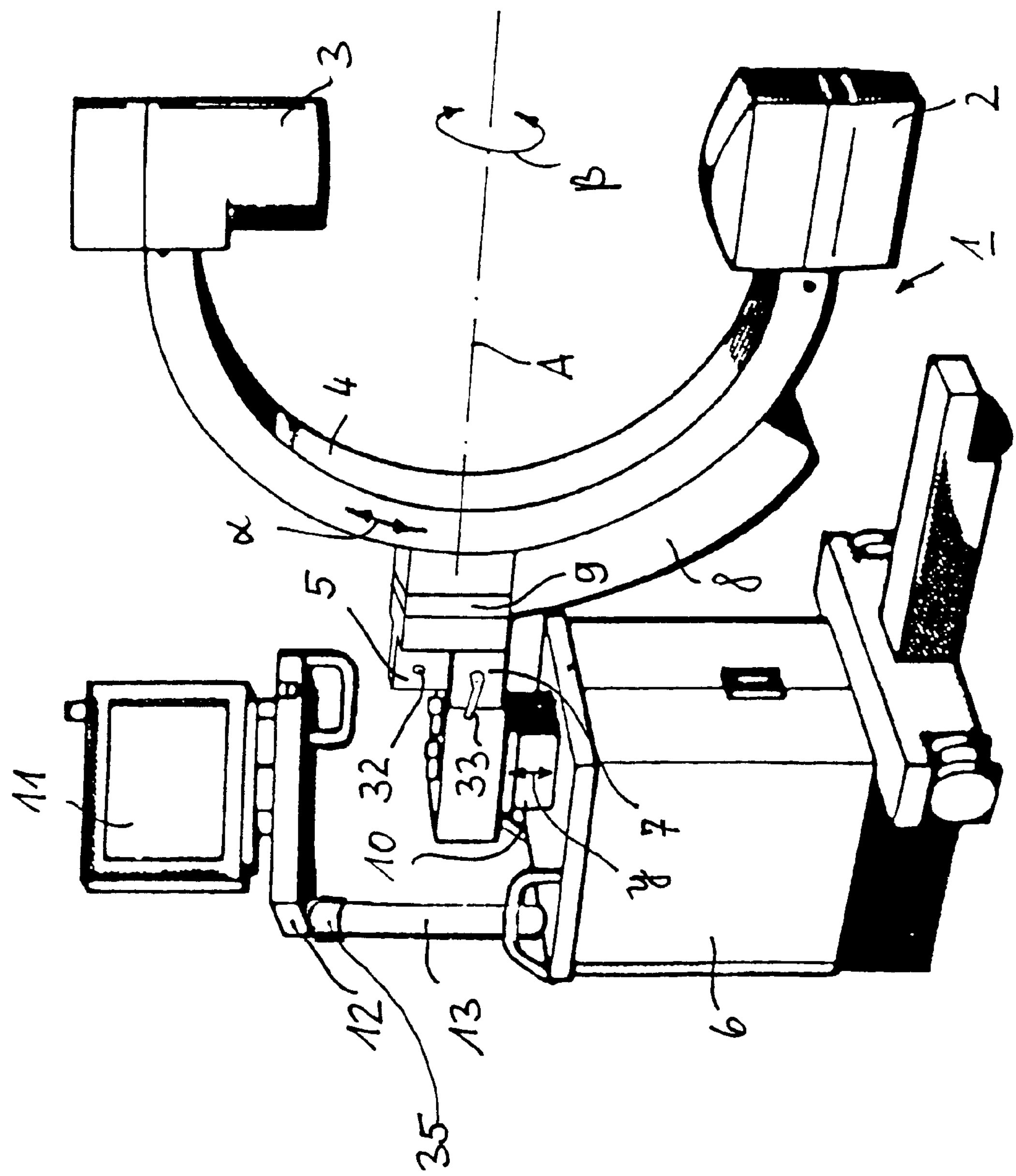
FIG. 1 shows a perspective view of an inventive X-ray examination apparatus in a first operating state.

As shown in FIG. 1, the inventive X-ray examination apparatus has an X-ray diagnostic assembly including an X-ray source 2 and a beam receiver, i.e. an X-ray image intensifier 3, attached opposite one another on a C-shaped curved carrier 4.

This carrier 4 is attached by means of a first coupling part 5 to a mobile (i.e. movable by means of wheels) base unit 6. The base unit 6 has a second coupling part 7 that mates with the first coupling part 5 of the carrier 4, so that the carrier 4 is detachably mounted to the base unit 6.

Articulated linkages 8 and 9 are located between the first coupling part 5 and the carrier 4, which enable displacement of the carrier 4 along its circumference in the direction of the curved double arrow $\alpha$, and around an axis A that runs through the midpoint of the curvature of the bearer 4 and lies in the center plane of the carrier 4 in the direction of the curved double arrow $\beta$.

The second coupling part 7 is attached to a vertically oriented support 10, which is mounted in the base unit 6 so as to be movable in the direction of the double arrow y, so that a height adjustment of the carrier 4, including the X-ray diagnostic assembly 1, is possible.

An X-ray image video chain is connected downstream from the X-ray image intensifier 3, and includes a monitor 11 that is attached to a base plate 12, which is in turn mounted detachably, e.g. by means of a bayonet-type coupling 35, to a holder 13 connected to the base unit 6.

The components required for the operation of the X-ray diagnostic assembly, e.g. a high-voltage generator for the X-ray source 2 and the video electronics, are housed in the base unit 6 in a known way which need not be shown. The cables connecting the X-ray source 2, the X-ray image intensifier 3 and the monitor 11 with these components are not shown in FIG. 1, for clarity.

From the above statements it is clear that the inventive X-ray examination apparatus can be used and operated in the manner of a conventional mobile X-ray apparatus.

Figure 2:
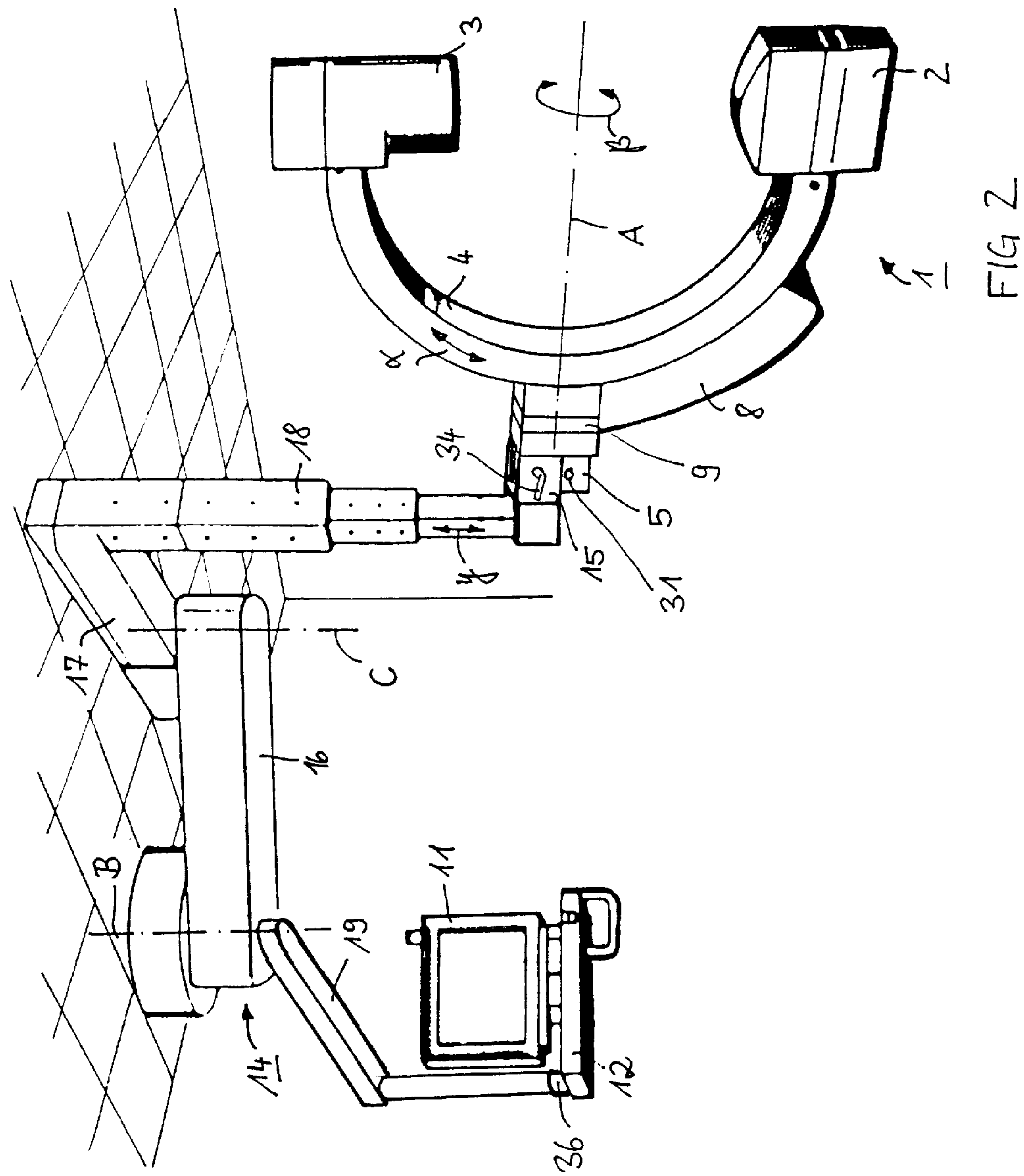
FIG. 2 shows the X-ray examination apparatus according to FIG. 1 in a second operating state, in a perspective view.

In contrast to conventional devices of this sort, however, the carrier 4 of the inventive X-ray examination apparatus can be separated from the base unit 6, and as shown in FIG. 2 can be attached by means of its first coupling part 5 to a stationary support 14, which in the case of the exemplary embodiment shown can be a ceiling support having a third coupling part 15 that permits detachable attachment of the carrier 4 to the support 14.

The support 14 has a first arm 16 that is rotatably attached to the ceiling of the room containing the X-ray examination apparatus, so as to be rotatable about a vertical axis B. A second arm 17 is attached to the free end of the first arm 16 so as to be rotatable about a likewise vertical axis C. A vertically oriented telescoping part 18 is attached at the free end of the second arm 17, and the third coupling part 15 is attached to the free end of this telescoping part 18.

The carrier 4 thus can be positioned freely in space within the limits given by the dimensions and the displacement range of the support 14, whereby, among other things, the displacement possibilities are again in the directions of the double arrows y, $\alpha$ and $\beta$.

The support 14 also has an angled mount 19 that is likewise rotatable about the axis B, to which the base plate 12 that supports the monitor 11 can be detachably attached as needed, e.g. by means of a bayonet-type coupling 36, as is shown in FIG. 2.

The base unit 6, which is placed off at a side so that it does not pose a hindrance, as well as the cables connecting this unit with the X-ray source 2, the X-ray image intensifier 3 and the monitor 11, are not shown in FIG. 2 for clarity.

As can be seen in FIG. 3, the second and the third coupling parts 7 and 15 are identical in their respective regions provided for cooperation with the first coupling part 5; namely, they are fork-shaped. The construction of the second and third coupling parts 7 and 15, identical in the region cited, is illustrated in FIG. 3 in that only one fork-shaped coupling part is shown, and is provided with reference characters 7 and 15. In order to produce the fork-shaped construction, the second and third coupling parts 7 and 15 each are provided with fork arms 20 and 21, through which bores 22 and 23 extend that are aligned with one another.

In its region provided for cooperation with the second and the third coupling parts 7 and 15, the first coupling part 5 has a block-shaped projection 24 that is dimensioned so that it can be introduced without play into the space located between the fork arms 20 and 21. In addition, the dimensions of the coupling parts 5, 7 and 15 are selected so that when the first coupling part 5 is introduced into the second or third coupling part 7 or 15, the frontal surface 25 of the projection 24 of the first coupling part 5 contacts the base surface 26, located between the fork arms 20 and 21, of the second or third coupling part 7 or 15, and/or the surfaces 27 and 28 of the first coupling part 5 (i.e. surfaces of the projection 24) contact the frontal surfaces 29 and 30 of the fork arms 20 and 21 of the second or third coupling parts 7 and 15.

As can be seen from FIG. 3, the height H of the projection 24 is at least equal to twice the height h of the fork arms 20 and 21. The projection 24 of the first coupling part 5 is provided with two bores 31 and 32, which have the same diameter as the bores 22 and 23 of the second and third coupling parts 7 and 15. The bores 31 and 32 are disposed so that the bore 31 is aligned with the bores 22 and 23 of the second coupling part 7, when the projection 24 of the first coupling part is introduced between the fork arms 20 and 21 of the second coupling part 7 thereby causing, as can also be seen in FIG. 1, the lower edge of the projection 24 to terminate flush with the lower edges of the fork arms 20 and 21. In order to secure the connection between the first and the second coupling parts 5 and 7, a mounting pin 33 is provided that is introduced into the bores 22, 23 and 31.

When the carrier 4 is set on the second coupling part 7 of the base unit 6, the projection 24 thus projects sufficiently upwardly from the second coupling part 7 so as to permit the third coupling part 15 to be brought into engagement with the projection 24. This is very advantageous because it produces a simple way of decoupling the carrier 4 from the base unit 6 and coupling it to the support 14. For this purpose, it is necessary only to orient the base unit 6 and the support 14 relative to one another so that the third coupling part 15 can be brought into engagement with the projection 24, and an additional mounting pin 34 can be introduced into the bores 22, 23 and 32. It is then necessary only to withdraw the mounting pin 34 in order to enable removal of the base unit 6.

If the carrier 4 is to be decoupled from the support 14 and coupled to the base unit 6, one proceeds in an analogous but reverse manner.

In the case of the exemplary embodiment, a ceiling support is used as the support 14, however, a floor support can alternately be used. In some circumstances, it is possible to provide ceiling supports in some operating rooms or treatment rooms and floor supports in others.

Moreover, the carrier 4 need not be constructed in a C-shape, as in the case of the exemplary embodiment. Rather, a U-shaped carrier, of a known type can alternatively be provided.

Also, an additional medical device can be removably attached to the base unit 6, e.g., in a way known from German OS 41 30 761, such as a source of acoustic waves.

The construction of the coupling parts 5, 7 and 15, described in connection with the exemplary embodiment, is to be understood only as an example. Other constructions of the coupling parts are possible.

In the case of the exemplary embodiment, an X-ray image intensifer 3 is provided as the beam receiver, to which an X-ray video chain is subsequently connected. Other beam receivers, e.g. flat semiconductor detectors or standard X-ray film cartridges, can also be provided.

Although modifications and changes may be suggested by those skilled in the art, it is the intention of the inventors to embody within the patent warranted hereon all changes and modifications as reasonably and properly come within the scope of their contribution to the art.

I claim as my invention:

1. An X-ray examination apparatus comprising: an X-ray diagnostic assembly for producing an X-ray image, said X-ray diagnostic assembly having a carrier with opposite ends, with an X-ray source and a beam receiver respectively mounted at said opposite ends, said carrier having a first coupling part selectively engageable with one of a second coupling part and a third coupling part at a time;

a mobile base unit containing a plurality of components electrically connected to said X-ray diagnostic assembly for operating said X-ray diagnostic assembly, said mobile base unit carrying said second coupling part, said second coupling part being releasably engageable with said first coupling part for temporarily allowing production of said X-ray image by said X-ray diagnostic assembly as a mobile diagnostic assembly; and at least one support for a stationary mounting in an examination room, carrying said third coupling part, said third coupling part releasably engageable with said first coupling part for temporarily allowing production of said X-ray image by said X-ray diagnostic assembly as a stationary diagnostic assembly.

2. An X-ray examination apparatus as claimed in claim 1 further comprising articulated linkage means, connected between said first coupling part and said carrier, for positioning said carrier relative to said first coupling part.

3. An X-ray examination apparatus as claimed in claim 1 wherein said beam receiver comprises an X-ray image intensifier, and said X-ray examination apparatus further comprising a video chain connected to said X-ray image intensifier and including a monitor attached to said base unit.

4. An X-ray examination apparatus as claimed in claim 3 further comprising means for detachably mounting said monitor on said base unit.

5. An X-ray examination apparatus as claimed in claim 1 wherein said second coupling part has a second coupling part region which engages said first coupling part and wherein said third coupling part has a third coupling part region which engages said first coupling part, said second coupling part region and said third coupling part region being identical.

6. An X-ray examination apparatus as claimed in claim 1 wherein said carrier comprises a C-arm.

* * * * *